United States Patent
Bell et al.

(10) Patent No.: US 9,505,688 B2
(45) Date of Patent: Nov. 29, 2016

(54) PROCESS FOR THE PREPARATION OF HIGH PURITY NORBORNENE ALKANOLS AND DERIVATIVES THEREOF

(71) Applicant: PROMERUS, LLC, Brecksville, OH (US)

(72) Inventors: Andrew Bell, Brecksville, OH (US); Dane Jablonski, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 0 days.

(21) Appl. No.: 15/162,805

(22) Filed: May 24, 2016

(65) Prior Publication Data

US 2016/0264498 A1     Sep. 15, 2016

Related U.S. Application Data

(62) Division of application No. 14/439,182, filed as application No. PCT/US2013/074397 on Dec. 11, 2013, now Pat. No. 9,382,271.

(60) Provisional application No. 61/739,119, filed on Dec. 19, 2012.

(51) Int. Cl.

| | |
|---|---|
| *C07C 29/128* | (2006.01) |
| *C07C 67/293* | (2006.01) |
| *C07F 7/18* | (2006.01) |
| *C07C 67/02* | (2006.01) |
| *B01J 31/04* | (2006.01) |
| *C07C 67/54* | (2006.01) |

(52) U.S. Cl.
CPC ............ *C07C 29/1285* (2013.01); *B01J 31/04* (2013.01); *C07C 67/02* (2013.01); *C07C 67/293* (2013.01); *C07C 67/54* (2013.01); *C07F 7/188* (2013.01); *C07F 7/1848* (2013.01); *B01J 2231/44* (2013.01); *B01J 2531/004* (2013.01); *C07C 2102/42* (2013.01); *C07C 2103/40* (2013.01); *C07C 2103/54* (2013.01)

(58) Field of Classification Search
None
See application file for complete search history.

(56) References Cited

FOREIGN PATENT DOCUMENTS

| | | | |
|---|---|---|---|
| JP | 2003055284 | * | 2/2003 |
| JP | 2008031304 A | | 2/2014 |
| WO | WO 2004/007587 A1 | | 1/2004 |
| WO | 2009061723 | * | 5/2009 |
| WO | WO 2009061723 A1 | | 5/2009 |

OTHER PUBLICATIONS

Database Caplus Chemical Abstracts Service, Columbus, Ohio, US; Database Accession No. 113:211434, Abstract of Smagin et al., Osn. Organ. Sintez i Neftekhimiya, Yaroslavl (1989), (25), 57-61.*
Chapter 20: Carboxylic Acid Derivatives, Nucleophilic Acyl Substitution <http://www.mhhe.com/physsci/chemistry/carey/student/olc/graphics/carey04oc/ref/ch2Oreactionsesters.html> visited Aug. 5, 2015.*
Machine Translation of JP 2003055284, 2003.*
M. K. Mamedov, "Synthesis of New Perfumes, the Esters of 2-Bicyclo[2.2.1]heptylmethanol," Russian Journal of Organic Chemistry, vol. 34, No. 2, 1998, pp. 178-182, Translated from Zhurnal Organicheskoi Khimii, vol. 34, No. 2, 1998, pp. 206-210.

* cited by examiner

*Primary Examiner* — Karl J Puttlitz
(74) *Attorney, Agent, or Firm* — Balaram Gupta

(57) ABSTRACT

A process for the preparation of a variety of high purity norbornene alkanol monomers and their derivatives is disclosed and claimed. Specifically, a process for the preparation of industrial scale high purity norbornene methanol and its silyl ether derivative is disclosed and claimed. The high purity monomers prepared in accordance with the process of this invention are useful in a variety of applications including but not limited to the preparation of high quality and high purity polynorbornenes having utility in a variety of electronic applications, among various other applications.

17 Claims, No Drawings

PROCESS FOR THE PREPARATION OF HIGH PURITY NORBORNENE ALKANOLS AND DERIVATIVES THEREOF

CROSS REFERENCE TO RELATED APPLICATIONS

This application is a divisional of U.S. application Ser. No. 14/439,182, filed Apr. 28, 2015, now allowed, which is a national phase application of PCT Application No. PCT/US2013/074397, filed Dec. 11, 2013, and published as International Publication No. WO 2014/099546A1 on Jun. 26, 2014, and which claims the benefit of U.S. Provisional Application No. 61/739,119, filed Dec. 19, 2012, each of which is incorporated herein by reference in its entirety.

TECHNICAL FIELD

Embodiments of the present invention relate to an industrial scale process for the preparation of norbornene alkanols and their derivatives. More specifically, such embodiments relate to a process for the preparation of a variety of high purity norbornene alkanols and the corresponding silyl ether derivatives, which are useful in a variety of industrial applications including as starting materials in the manufacture of electronic/optoelectronic polymeric materials.

BACKGROUND

Functionalized norbornene monomers are extensively used in the preparation of polymers having a wide variety of applications especially in the electronic industry. In particular, various electronic materials utilize polynorbornenes because of their unique film forming properties supplemented with desirable electronic material properties. Such applications include, among others, their use as dielectrics, photoresists, protective layers and liquid crystal display layers. However, as these applications require very high purity materials, it is particularly important that various functionalized norbornene monomers are free of any impurity that might make it difficult to form high molecular weight polymers.

Recently, there has been a considerable interest in the use of polynorbornene alkanol derivatives in such electronic applications as a retardation film having utility in liquid crystal displays (LCDs), see for example, PCT International Application No. WO 2008/130186.

U.S. Pat. No. 7,541,073 discloses alignment films for LCD which are made from photoreactive polymers containing polynorbornene alkanol derivatives. However, the reported yields of the monomer, norbornene methanol, is low making it unsuitable for an industrial operation. Furthermore, it is known that it is extremely difficult to make a high purity norbornene alkanol, such as, norbornene methanol having purity in excess of 95%. It is particularly difficult to prepare a norbornene alkanol in the absence of any of the corresponding hydrogenated versions, such as for example norbornane methanol. Particularly it has been reported that norbornene methanol readily undergoes hydrogenation to form norbornane methanol, see, for example, Gasanov, Russian Journal of Organic Chemistry, Vol. 39. No. 7, 2003, pp. 947-951.

It has also been reported that certain norbornene alkanol benzoates can be prepared by the reaction of dicyclopentadiene with the corresponding alkenol benzoate esters. However, the reported yields are low and use of benzoate esters in an industrial scale may not be suitable for the preparation of various norbornene alkanol derivatives, see, Guseinov et al., Doklady Akademiya Nauk Azerbaidzhanskoi SSR, 35(10), 45-8; (1979).

In view of the foregoing, there is a need to develop industrially viable processes to prepare high purity norbornene alkanol monomers.

Other objects and further scope of the applicability of the present invention will become apparent from the detailed description that follows.

DETAILED DESCRIPTION

The terms as used herein have the following meanings:

As used herein, the articles "a," "an," and "the" include plural referents unless otherwise expressly and unequivocally limited to one referent.

As used herein, "hydrocarbyl" refers to a moiety or a group that contains only carbon and hydrogen, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term perhalocarbyl refers to a hydrocarbyl group where all of the hydrogens have been replaced by a halogen.

As used herein, the expression "alkyl," such as "$(C_1-C_6)$alkyl" includes methyl and ethyl groups, and straight-chained or branched propyl, butyl, pentyl and hexyl groups. Particular alkyl groups are methyl, ethyl, n-propyl, isopropyl, tert-butyl, and so on. Derived expressions such as "$(C_1-C_6)$alkoxy", "$(C_1-C_6)$thioalkyl", "$(C_1-C_6)$alkoxy$(C_1-C_6)$alkyl", "hydroxy$(C_1-C_6)$alkyl", "$(C_1-C_6)$alkylcarbonyl", "$(C_1-C_6)$alkoxycarbonyl$(C_1-C_6)$alkyl", "$(C_1-C_6)$alkoxycarbonyl", "amino$(C_1-C_6)$alkyl", "$(C_1-C_6)$alkylamino", "$(C_1-C_6)$alkylcarbamoyl$(C_1-C_6)$alkyl", "$(C_1-C_6)$dialkylcarbamoyl$(C_1-C_4)$alkyl" "mono- or di-$(C_1-C_6)$alkylamino$(C_1-C_6)$alkyl", "amino$(C_1-C_6)$alkylcarbonyl" "diphenyl$(C_1-C_6)$alkyl", "phenyl$(C_1-C_6)$alkyl", "phenylcarboyl$(C_1-C_6)$alkyl" and "phenoxy$(C_1-C_6)$alkyl" are to be construed accordingly. Further, as used herein "lower alkyl" shall mean generally $(C_1-C_6)$alkyl.

As used herein, the expression "cycloalkyl" includes all of the known cyclic radicals. Representative examples of "cycloalkyl" include without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_2-C_6)$alkenyl" includes ethenyl and straight-chained or branched propenyl, butenyl, pentenyl and hexenyl groups. Similarly, the expression "$(C_2-C_6)$alkynyl" includes ethynyl and propynyl, and straight-chained or branched butynyl, pentynyl and hexynyl groups. Derived expressions, such as "$(C_5-C_{12})$cycloalkenyl", "$(C_2-C_6)$alkenol", "$(C_5-C_{12})$cycloalkenol", are to be construed accordingly.

As used herein the expression "$(C_1-C_4)$acyl" shall have the same meaning as "$(C_1-C_4)$alkanoyl", which can also be represented structurally as "R—CO—," where R is a $(C_1-C_3)$alkyl as defined herein. Additionally, "$(C_1-C_3)$alkylcarbonyl" shall mean same as $(C_1-C_4)$acyl. Specifically, "$(C_1-C_4)$acyl" shall mean formyl, acetyl or ethanoyl, propanoyl, n-butanoyl, etc. Derived expressions such as "$(C_1-C_4)$acyloxy" and "$(C_1-C_4)$acyloxyalkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1\text{-}C_6)$perfluoroalkoxy", is to be construed accordingly.

As used herein, the expression "$(C_6\text{-}C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$(C_6\text{-}C_{10})$arylsulfonyl," is to be construed accordingly.

As used herein, the expression "$(C_6\text{-}C_{10})$aryl$(C_1\text{-}C_4)$alkyl" means that the $(C_6\text{-}C_{10})$aryl as defined herein is further attached to $(C_1\text{-}C_4)$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrroyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1\text{-}6}$alkyl, $C_{2\text{-}6}$alkenyl, $C_{1\text{-}6}$perfluoroalkyl, phenyl, hydroxy, $-CO_2H$, an ester, an amide, $C_1\text{-}C_6$alkoxy, $C_1\text{-}C_6$thioalkyl, $C_1\text{-}C_6$perfluoroalkoxy, $-NH_2$, Cl, Br, I, F, $-NH$-lower alkyl, and $-N$(lower alkyl)$_2$. However, any of the other suitable substituents known to one skilled in the art can also be used in these embodiments.

In addition, unless otherwise indicated, all numbers, values and/or expressions referring to quantities of ingredients, reaction conditions, temperature, pressure, time, and the like, that are used herein are to be understood as modified in all instances by the term "about" to take into account the uncertainties associated with determining such values.

Further, any numerical ranges disclosed herein will be understood to be continuous, and inclusive of every value between the minimum and maximum values of each range. Unless expressly indicated otherwise, such numerical ranges are approximations that are reflective of the various uncertainties of measurement encountered in obtaining such values. Accordingly, unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, include but not limited to, 1 to 6.1, 3.5 to 7.8, and 5.5 to 10.

The features that characterize embodiments of the present invention are pointed out with particularity in the claims, which form a part of this disclosure. These and other features of such embodiments, their operating advantages and uses will be more fully understood from the description of such embodiments herein below and the examples that follow.

Thus, in accordance with the practice of this invention there is provided a process for the preparation of a compound of formula (I):

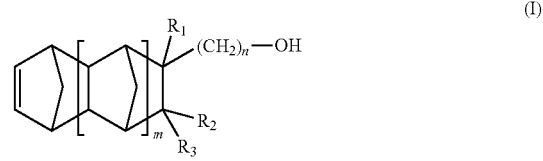

(I)

wherein
n is an integer from 1 to 10, inclusive, and where one or more of $CH_2$ is optionally substituted with $C_1\text{-}C_{10}$-alkyl or $C_1\text{-}C_{10}$-perfluoroalkyl;
m is an integer from 0 to 2, inclusive;
$R_1$, $R_2$ and $R_3$ are the same or different and independently of each other selected from hydrogen, halogen and hydrocarbyl, where hydrocarbyl is selected from methyl, ethyl, linear or branched $C_3\text{-}C_{12}$-alkyl, $C_3\text{-}C_{12}$-cycloalkyl, $C_6\text{-}C_{12}$-bicycloalkyl, $C_7\text{-}C_{14}$-tricycloalkyl, $C_6\text{-}C_{10\text{-}aryl}$, $C_6\text{-}C_{10}$-aryl-$C_1$-$C_3$-alkyl, $C_5\text{-}C_{10}$-heteroaryl, $C_5\text{-}C_{10}$-heteroaryl-$C_1$-$C_3$-alkyl, $C_1\text{-}C_{12}$-alkoxy, $C_3\text{-}C_{12}$-cycloalkoxy, $C_6\text{-}C_{12}$-bicycloalkoxy, $C_7\text{-}C_{14}$-tricycloalkoxy, $C_6\text{-}C_{10}$-aryloxy-$C_1$-$C_3$-alkyl, $C_5\text{-}C_{10}$-heteroaryloxy-$C_1$-$C_3$-alkyl, $C_6\text{-}C_{10}$-aryloxy, $C_5\text{-}C_{10}$-heteroaryloxy and $C_1\text{-}C_6$-acyloxy;
comprising:
reacting dicyclopentadiene with a compound of formula (II):

wherein
R is $-OCOC_1\text{-}C_6$-alkyl, $-CHO$, $-CN$, $-OC_1\text{-}C_6$-alkyl, $-OCH_2Ph$, $-OSO_2R_4$, where $R_4$ is $C_1\text{-}C_4$-alkyl or $C_6\text{-}C_{12}$-aryl;
at a suitable temperature and conditions to form a compound of formula (III):

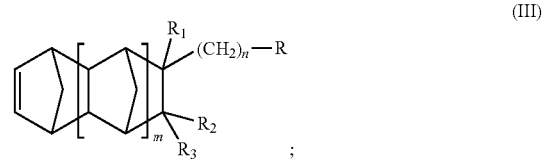

(III)

and
subjecting compound of formula (III) to suitable transformation reaction to form the compound of formula (I).

Thus in accordance with the practice of this invention it has now been found that various substituted alkene derivatives as represented by the compound of formula (II) can now be reacted with dicyclopentadiene (DCPD) to form a compound of formula (III) which can further be converted to norbornene alkanol as represented by the compound of formula (IA), where m=0, as summarized in Scheme I.

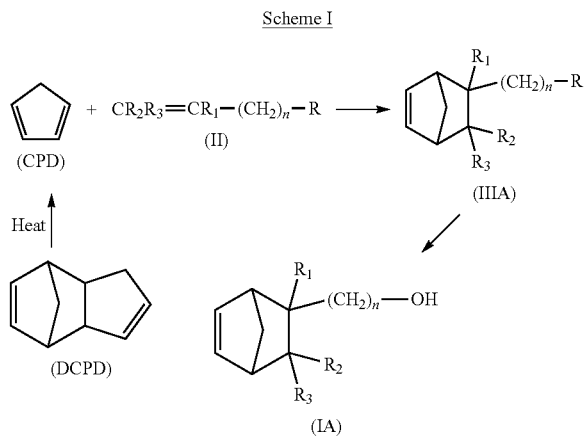

Scheme I

As depicted in Scheme I, in accordance with the process of this invention, cyclopentadiene (CPD), generated from its dimer form DCPD, is reacted first with a substituted alkene derivative as represented by the compound of formula (II). This reaction can be carried out using any of the known reaction conditions so as to form a compound of formula (IIIA). Such suitable reaction conditions include but are not limited to ambient, super-ambient or sub-ambient reaction temperature and pressure conditions for a sufficient period of time. Typically such reactions are carried at elevated temperatures in a closed reaction system at autogenous pressure conditions. That is to say, the pressure produced itself by the heating of the reactants in a closed reaction vessel. For example, such reactions can be carried out in a suitable closed pressure reactor system at a temperature range of from about 130° C. to about 260° C. In some other embodiments, the reaction can be carried out at a temperature range of from about 200° C. to about 240° C.; and in some other embodiments the reaction can be carried out at a temperature range of from about 180° C. to about 240° C.; and yet in some other embodiments at a temperature range of from about 210° C. to about 230° C. In some other embodiments the reaction can be carried out at a temperature of about 220° C. Suitable reactor systems include but are not limited to closed tubular reactor, pressure vessels, such as, Parr reactor or such suitable vessels and/or reactors constructed of glass, glass-lined metal (or other suitably lined metal including quartz or TEFLON® (polytetrafluoroethylene)) or metal, including but not limited to stainless steel, HASTELLOY® (an alloy comprising Ni 57.0%, Mo 16.0%, Cr 15.5%, Fe 5.5% and W 3.8%), INCONEL® (Nickel-Chromium alloy), and the like.

In general, the reaction of DCPD with a compound of formula (II) takes place first by the breaking down of DCPD into monomeric cyclopentadiene (CPD) and then reacting with the compound of formula (II). Generally, it has now been found that employing excess molar amounts of compound of formula (II) with respect to CPD results in higher yields of the compound of formula (III). Typically, the molar ratio of CPD:compound of formula (II) can range from about 1:1 to about 1:8, from about 1:1 to about 1:5 and from about 1:1 to about 1:4. However, any other molar ratios that would bring about the reaction can also be used, such as for example, a ratio of from about 2:1 to 1:2 can also be used.

For compounds of formula (I), where m=1 or 2, the compound of formula (IIIA) can further be reacted sequentially with additional quantities of CPD (or DCPD which when heated to a temperature of about 150° C. undergoes a retro Diels-Alder reaction to form CPD) to obtain the compound of formula (I), where m=1 or 2.

Generally, the reaction is carried out neat, i.e., without any solvents, and/or other agents, such as catalysts, and the like. However, depending upon the type of substituted alkene derivative of formula (II) employed suitable solvents can also be used in some situations. Exemplary solvents include without any limitation, hydrocarbon solvents, such as hexane, heptane, petroleum ether, benzene, toluene, xylene, and the like, halohydrocarbon solvents, such as dichloromethane, 1,1-dichloroethane, chloroform, carbon tetrachloride, and the like. Other suitable solvents include dimethyl sulfoxide (DMSO), dimethyl formamide (DMF), dimethyl acetamide (DMAc), acetone, methyl ethyl ketone (MEK), among others.

Generally, the progress of the reaction can be monitored by removing aliquots from the reactor and analyzing by suitable methods such as thin layer chromatography (TLC), gas chromatography (GC), liquid chromatography (LC) or high performance liquid chromatography (HPLC), or a combination of GC/mass spectroscopy (MS), LC/MS, among other known techniques.

Advantageously, it has now been found that by practice of the present invention it is now possible to obtain the compound of formula (I) in very high purity. As used herein "high purity" means the product independent of other impurities particularly where the norbornene moiety is hydrogenated to norbornane. That is to say the compound of formula (I) is essentially free of the corresponding norbornane derivative. In one of the embodiments, the compound of formula (I) obtained from the process of this invention is of at least 99 percent purity. In another embodiment, the compound of formula (I) obtained from the process of this invention is of at least 99.4 percent purity. In another embodiment, the compound of formula (I) obtained from the process of this invention is of at least 99.8 percent purity.

It should further be noted that any of the prior art methods as further exemplified below by specific examples produces a compound of formula (I) of low purity by the direct reaction of CPD with any of the corresponding alkenols. As noted, this reaction not only results in low purity but also results in very low yields and therefore unsuitable for any industrial operation. Generally, it has been found that any functional group that facilitates hydrogen transfer results in undesirable by-products. For example, as demonstrated herein by comparative examples either use of alkenol as a co-reactant and/or use of alcohol solvents with CPD results in undesirable by-products presumably resulting due to hydrogen transfer reactions. On the other hand, as also demonstrated herein, the process of this invention produces surprisingly a very high purity compound of formula (III) which can very readily be converted into compound of formula (I) as further discussed below.

Any of the known substituted alkene derivatives of formula (II) can be employed for the preparation of compound of formula (III). As noted, such substituted alkene derivatives of formula (II) include without any limitation, any of the aliphatic acid esters. Exemplary aliphatic acid esters include without any limitation acetate, propionate, n-butyrate, iso-butyrate, n-pentanoate, and the like. Other aliphatic acid esters such as cycloaliphatic acid esters, such as cyclopentane carboxylate, cyclohexane carboxylate, etc., can also be employed. Other substituted alkene derivatives include the corresponding aldehyde, —CHO, or nitrile, —CN, which can be converted to alcohol function after the addition reaction with CPD as represented in Scheme I. Other substituted alkene derivatives include various ethers, including ethers with various $C_1$-$C_6$-alkanols to form the corresponding —$OC_1$-$C_6$-alkyl ethers. Exemplary alkanols that can be employed to form the corresponding ethers include, among others, methanol, ethanol, n-propanol, isopropanol, n-butanol, iso-butanol, tert-butanol, all isomeric forms of pentanol or hexanol, and the like. Finally, other substituted alkene derivatives of formula (II) may also include various sulfonates of formula —$OSO_2R_4$, where $R_4$ is $C_1$-$C_4$-alkyl, $C_1$-$C_4$-perfluoroalkyl or $C_6$-$C_{12}$-aryl. Exemplary sulfonates include without any limitation methanesulfonate or mesylate, trifluoromethanesulfonate or triflate, ethanesulfonate, benzenesulfonate (besylate), p-toluenesulfonate (tosylate), and the like. It should further be noted that various alkene derivatives as described herein are formed by the protection of corresponding alcohol with a suitable protecting group. For examples of various such protecting groups including the ones described herein can be found in Greene, T. W.; Wuts, P. G. M. Protective Groups in Organic Synthesis" 4th Ed. (2007).

Many of the aforementioned substituted alkene derivatives of formula (II) are either commercially available or can be readily synthesized by any of the procedures known to one skilled in the art. For example, many of the alkenol esters of formula (II) are commercially available and/or can be readily prepared by the esterification reaction of the corresponding alcohol and the acid. Similarly, the alkenol ethers and the sulfonate esters can also be prepared by employing the suitable starting materials. The corresponding aldehyde or nitrile compounds, i.e., where R=CHO or CN can also be similarly prepared starting from appropriate starting materials and by employing any of the known literature procedures.

In one of the embodiments of the process of this invention, the substituted alkene derivative of formula (II) employed is allyl acetate, i.e., the compound of formula (II) wherein n is 1, R is $CH_3C(O)O$ and each of $R_1$, $R_2$ and $R_3$ is hydrogen. The compound of formula (IIIA) so formed, in this case, an ester, specifically an acetate can be subjected to a suitable trans-esterification agent in the presence of a catalyst to form compound of formula (IA), where n=1 and m=0.

Broadly speaking, the trans-esterification reaction in order to covert an ester compound of formula (III) to compound of formula (I) can be performed using any of the known procedures in the art. For example, such trans-esterification reactions can be carried out at a suitable temperature in the presence of a suitable acid or a base catalyst in a suitable solvent and a suitable trans-esterification agent. Suitable trans-esterification agent is an alcohol, such as methanol, ethanol, isopropanol, n-butanol, iso-butanol, and the like. Various other alcohols can also be employed. In one of the embodiments of this invention the alcohol used is methanol. Various other solvents can also be used in combination with aforementioned alcohol solvents. Specific example includes, petroleum ether, dichloromethane, methyl acetate, ethyl acetate, toluene, and the like.

Suitable base catalysts include but not limited to alkaline base, e.g., lithium, sodium, potassium or cesium hydroxide, alkoxide, carbonate, bicarbonate, and the like; an alkaline earth metal base, e.g., calcium or magnesium hydroxide, alkoxide, carbonate, bicarbonate and the like, and suitable inorganic or organic base, e.g., ammonia, trialkylamine, imidazole, and the like. Specific alkali bases include but not limited to lithium hydroxide, lithium methoxide, lithium ethoxide, lithium tert-butoxide, lithium carbonate, lithium bicarbonate, sodium hydroxide, sodium methoxide, sodium ethoxide, sodium tert-butoxide, sodium carbonate, sodium bicarbonate, potassium hydroxide, potassium methoxide, potassium ethoxide, potassium tert-butoxide, potassium carbonate, potassium bicarbonate, cesium hydroxide, cesium methoxide, cesium ethoxide, cesium tert-butoxide, cesium carbonate, cesium bicarbonate, calcium hydroxide, calcium methoxide, calcium ethoxide, calcium tert-butoxide, calcium carbonate, calcium bicarbonate, magnesium hydroxide, magnesium methoxide, magnesium ethoxide, magnesium tert-butoxide, magnesium carbonate, magnesium bicarbonate, ammonia, trimethylamine, triethylamine, imidazole, and any combination of mixtures thereof.

Suitable acid catalysts include but not limited to any of the known Bronsted acids, such as hydrochloric acid, hydrobromic acid, hydrofluoric acid, sulfuric acid, methanesulfonic acid, trifluoromethanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid, and the like. Any of the known Lewis acids can also be employed either alone or in combination with aforementioned Bronsted acids. Specific examples of Lewis acid include without any limitation, boron trifluoride, boron trichloride, aluminum chloride, antimony pentafluoride, and the like. Thus, in one of the embodiments of this invention the trans-esterification agent is an alcohol, such as methanol, and the catalyst employed is an acid, for example, sulfuric acid or a sulfonic acid such as methane sulfonic acid (MsOH) or p-toluenesulfonic acid (p-TsOH).

Generally, one or more of the aforementioned acid or base catalysts can be employed in catalytic amounts in the trans-esterification reaction. For example, the catalytic amounts of acid or base employed can vary from about 0.1 mole percent to about fifty mole percent when compared with the compound of formula (III). Generally, slightly larger mole percent of base catalyst is used when compared with the acid catalyst. That is when acid is used as the catalyst the amount of acid used can be as low as 0.1 mole percent. However, when base is used as the catalyst the amount can range from about 1 mole percent to about fifty mole percent. In some embodiments the catalyst used is a base catalyst and is employed from about 4 mole percent to about 20 mole percent and in some other embodiments from about 5 mole percent to about 10 mole percent. Thus in one of the embodiments of this invention the solvent used is methanol and the base used is sodium methoxide in the amount of about 8 mole percent when compared with compound of formula (III).

Generally, the trans-esterification reaction can be carried out at a broad temperature range that includes sub-ambient, ambient and super-ambient temperature ranges and depends upon the type of ester being employed. For example, in some embodiments, the temperature range can be from about 0° C. to 100° C. In some other embodiments the temperature range can be from about 20° C. to 80° C. In yet some other embodiments the temperature range can be from about 40° C. to 60° C. However, any of the other suitable temperature ranges can also be employed depending upon the starting materials as one of skill in the art would readily appreciate such modifications.

Similarly, if the addition product is a sulfonate ester, i.e., a compound of formula (III) wherein R is —OSO$_2$R$_4$, such sulfonate esters of formula (III) can also be converted to a compound of formula (I) by subjecting it to any of the acid or base catalyzed trans-esterification reaction as described above.

If the addition product formed is an ether, i.e., a compound of formula (III) wherein R is —OC$_1$-C$_6$-alkyl, such ethers can be cleaved to compound of formula (I) by employing any of the known literature procedures. Such ether cleavage reactions include acid catalyzed reactions as well as any of the known silyl agents which would cleave ethers to form the respective alcohols.

As noted, by practicing the process of this invention it is now possible to obtain compound of formula (I) in very high purity. Accordingly, the compound of formula (I) formed in one of the embodiments is exo-/endo-norbornene methanol of at least 99 percent purity.

In another embodiment of the process of this invention, the process further comprises:
reacting a compound of formula (I) with a silane of formula (IV):

R$_5$R$_6$R$_7$SiH          (IV)

wherein R$_5$, R$_6$ and R$_7$ are each independently of one another methyl, ethyl or linear or branched C$_3$-C$_9$-alkyl or substituted or unsubstituted C$_6$-C$_{14}$-aryl; and a suitable catalyst to obtain a compound of formula (V):

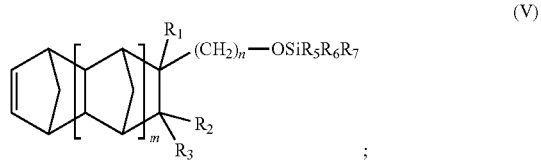

and
wherein the compound of formula (V) thus formed is of high purity.

Advantageously, it has now been found that the reaction of compound of formula (IV) with a compound of formula (I) can be carried out using a base as the catalyst, see, for example, Weickgenannt et al., Chem. Asian J. 2009, 4, 406-410. Various base catalysts that can be used in this reaction include all of the base catalysts which are employed for the trans-esterification and as enumerated hereinabove. Specifically, in one of the embodiments it has now been found that a suitable base catalyst is potassium tert-butoxide. However, as noted above, any of the other base catalysts as listed above can also be employed in this step.

In one of the embodiments, the compound of formula (V) thus formed is having: n is 1, each of R$_1$, R$_2$ and R$_3$ is hydrogen, R$_5$ is methyl, and each of R$_6$ and R$_7$ is phenyl. In another embodiment of this invention the compound of formula (V) thus formed is of high purity. Specifically, the purity of the compound of formula (V) is at least 99 percent. In another embodiment, the purity of the compound of formula (V) is at least 99.5 percent. In another embodiment, the purity of the compound of formula (V) is at least 99.8 percent. More specifically, the compound of formula (V) thus formed is (bicyclo[2.2.1]hept-5-en-2-ylmethoxy)(methyl)diphenylsilane and is of at least 99 percent purity. In another embodiment, the compound of formula (V) thus formed is (bicyclo[2.2.1]hept-5-en-2-ylmethoxy)(methyl)diphenylsilane and is of at least 99.8 percent purity.

In another embodiment of this invention there is also provided a process for the preparation of norbornene methanol of formula (IB):

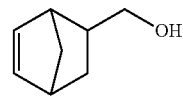

In this embodiment the process is comprised of: reacting dicyclopentadiene with allyl acetate at a temperature of from about 200° C. to about 240° C. for a sufficient period of time to form norbornene methyl acetate of formula (IIIB):

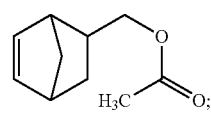

distilling so formed norbornene methyl acetate of formula (IIIB); and
subjecting said distilled norbornene methyl acetate (IIIB) to trans-esterification reaction in the presence of methanol and sodium methoxide at a temperature of from about 40° C. to about 50° C. to form norbornene methanol (IB) of purity of at least 99.8 percent. In this process, no hydrogenated norbornene methanol, i.e., norbornane methanol (NBaneCH$_2$OH), is generated.

In a further embodiment of this invention there is provided a process for the preparation of (bicyclo[2.2.1]hept-5-en-2-ylmethoxy)(methyl)diphenylsilane of formula (VB):

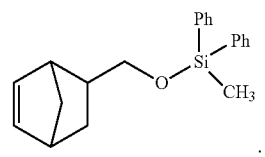

This embodiment encompasses: reacting dicyclopentadiene with allyl acetate at a temperature of from about 200° C. to about 240° C. for a sufficient period of time to form norbornene methyl acetate of formula (IIIB):

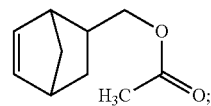

subjecting norbornene methyl acetate (IIIB) to trans-esterification reaction in the presence of methanol and sodium methoxide at a temperature of from about 40° C. to about 50° C. to form norbornene methanol (IB):

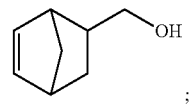

and
reacting norbornene methanol (IB) with methyldiphenylsilane in the presence of a suitable solvent and potassium tert-butoxide to obtain (bicyclo[2.2.1]hept-5-en-2-yl-methoxy)(methyl)diphenylsilane (VB) of at least 99.5 percent purity.

It should be noted that the process of this invention provides several hitherto unattainable advantages. More importantly, it should be noted that many of the literature procedures require use of various reagents, which unavoidably introduces certain impurities into the final product. For example, by employing the free alkenol as the starting material (i.e., R═OH in the compound of formula (II)), and following the literature procedure results in a compound of formula (I) of low purity. More importantly, as demonstrated by the following comparative examples any presence of protic sources such as alcohols results in the hydrogenation of compound of formula (I), which is always formed as a significant by-product and in most situations difficult to separate. That is to say, when compound of formula (I) is hydrogenated that results in the formation of corresponding norbornane compound having very similar physical properties such as boiling point.

In addition, the silylation procedure as described herein also offers a unique method to prepare compounds of formula (V) of very high purity. It should particularly be noted that many of the literature procedures require either acid or base conditions which results unavoidably in certain contaminants which are difficult to remove and are unsuitable impurities particularly in electronic applications. For example, it is well known in the literature to prepare silyl ether compounds by the reaction of alcohol with a suitable chlorosilane or a suitable silyl amine. For instance, Scheme II illustrates the preparation of a compound of the formula (VA) by the reaction of compound of formula (IA) either with diphenylmethylchlorosilane, or N,N,1-trimethyl-1,1-diphenylsilanamine. In both of these literature processes alkylammonium chloride is formed as a by-product, which requires laborious purification process to purify compound of formula (VA). On the other hand, the process of this invention provides an efficient industrially readily scalable process to prepare high purity silyl ether compounds of formula (V) and particularly the compound of formula (VA).

Scheme II

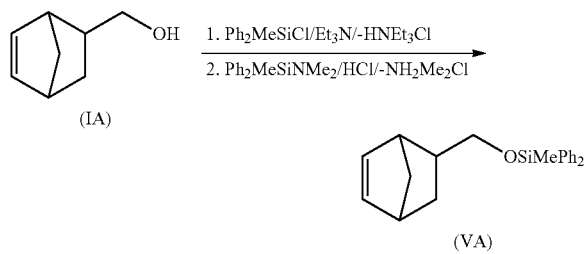

This invention is further illustrated by the following examples which are provided for illustration purposes and in no way limit the scope of the present invention.

Example 1

Exo-/Endo-Norbornene Methyl Acetate

Into a suitable high pressure tube reactor were placed allyl acetate and dicyclopentadiene (DCPD) at 4:1 molar ratio based on cyclopentadiene monomer, and heated in a hot oil bath maintained at 220° C., and maintained at that temperature for four hours. At the end of the reaction, the high pressure tube was removed from the bath and quenched in a wet ice bath. The tube was washed then with methanol and dichloromethane and weighed to verify that no leakage had occurred. The resultant crude monomer sample was analyzed by GC-MS, which showed about 7.5% unreacted allyl acetate, 10% exo-/endo-norbornene methanol, 82% exo-/endo-norbornene methyl acetate and 0.6% (1,2,3,4,4a,5,8,8a-octahydro-1,4:5,8-dimethanonaphthalen-2-yl)methanol. Fractional distillation of the crude mixture resulted in the isolation of norbornene methyl acetate of greater than >99.6% purity.

The GC-MS analysis was performed on an Altech EC-5 column, 30 m, 0.25 mm ID, 0.25 μm film; Inlet-F: 250, MS source: 230° C., electron ionization. The GC conditions used are as follows: Gradient: 45° C. to 120° C. at 10° C./min, then heat at 40° C./min to 300° C., hold 2 min at 300° C.

Example 2

Exo-/Endo-Norbornene Methanol

Into a suitably sized and jacketed reactor were placed a mixture of exo-/endo-norbornene methylacetate (≥99.6% purity, 4.8 kg) and methanol (11.2 kg). The reactor was equipped with an agitator, overhead condenser, overhead condensate receiver tank, and feed tank with metering pump. The temperature of the reactor was controlled by a dedicated oil circulation unit; reactor pressure was manually controlled, with nitrogen addition to increase pressure and vent takeoff to decrease pressure.

The reactor was purged with nitrogen using three pressure/vacuum swings to remove any oxygen in the reactor headspace. After this nitrogen purge process, the reactor was left in a fully vented mode through the overhead condenser and receiver system, and then heated to the initial reaction temperature (45° C.). A catalyst solution consisting of sodium methoxide in methanol (25 wt %, 0.125 kg) was added to the glass feed tank and then metered into the reactor over a 15 minute period (addition rate 8.33 g/min), while maintaining reactor temperature (45° C.). After completion of the catalyst metered addition, the reactor was maintained at temperature (45° C.) for an additional 1.75 hours.

After completion of the reaction process, the reactor was heated to solvent stripping temperature (60-68° C.) in vented mode, and a mixture of methanol/methylacetate (4 kg) was flashed overhead and collected in the overhead receiver tank. Additional methanol (4 kg) was transferred to the reactor, and a second solvent stripping operation was conducted to remove a mixture of methanol/methylacetate (4 kg). Finally, a third solvent stripping operation was conducted to remove a mixture of methanol/methylacetate (6 kg). After completion of this solvent stripping process, acetic acid (0.04 kg) was added to the reaction concentrate, which was then transferred out of the reactor and analyzed via GC to confirm that the trans-esterification reaction was complete. Composition of the reaction concentrate was as follows: norbornene methanol 83%, norbornene methyl acetate trace amounts, methanol 17% and MeOAc trace amounts.

The norbornene methanol reaction concentrate (6 kg) was then charged to a suitably equipped vacuum distillation system consisting of a still pot with electric heating mantle, distillation column with stainless steel structured packing (4 theoretical plates), reflux splitter, water cooled condenser, overhead condensate receiver, and vacuum pump. Still pot temperature was controlled by adjusting the heat input on the heating mantle, and system vacuum was controlled by adjusting vacuum pressure at the overhead receiver. The still pot was initially heated in fully vented mode until reflux conditions were established in the distillation column. The reflux splitter was then started at the desired reflux ratio and fractional distillation proceeded by periodically removing liquid fractions from the overhead receiver. GC analysis was used to determine composition of the overhead fractions. Still pot temperature, overhead receiver vacuum, and reflux ratio were adjusted as needed to affect composition of the overhead stream. Initial overhead fractions contained primarily methanol with trace amounts of methylacetate. After removal of these solvents, high purity norbornene methanol was then distilled overhead under the following conditions: overhead temperature (70-75° C.), vacuum (4-5 mm Hg), and reflux ratio (2:1). The distillation process was terminated once the majority of the product had been removed from the still pot. Approximately 90% of the contained norbornene methanol in the starting mixture was recovered as high-purity (≥99.8% assay) product, with trace amount of norbornene methyl acetate (<0.1%) and non-detectable levels of norbornane methanol (NBAMeOH).

The GC analysis was performed on an Ultra 1 (cross-linked methyl siloxane) column, 25 m, 0.2 mm ID, 0.33 µm film. Initial Conditions: 70° C., hold 1.0 min.; Gradient Conditions: 70° C. to 240° C. @10° C./min.; Final Conditions: 240° C., hold 10.0 min. Injector: 200° C. Detector: 250° C. (FID). GC retention times: NBMeOH 7.1-7.3 min., NBAMeOH 7.5-7.6 min., and NBMeOAc 8.8-8.9 min.

Example 3

Exo-/Endo-(Norbornenylmethoxy)(Methyl)Diphenylsilane (NBMeOSiPh$_2$Me)

Into a suitably sized flask equipped with a mechanical stirrer, addition funnel, nitrogen inlet, and thermowell were placed norbornene methanol (NBMeOH, 99 g, 0.797 mol). Dry THF (300 ml) was syringed into the flask and then stirring was started. Potassium t-butoxide (3.3 g, 0.029 mol) was added. When the potassium t-butoxide had all dissolved to give a yellow solution, a water bath was set underneath the reaction flask. Diphenylmethylsilane (150.3 g, 0.756 mol) was added drop wise. After about ten minutes, hydrogen evolution began and the reaction temperature increased from 23° C. to 25° C. The diphenylmethylsilane was added at a steady drop rate to maintain moderate evolution of hydrogen. The addition was completed after about 50 minutes. The reaction temperature had climbed to 30° C. Within one minute, hydrogen evolution abruptly stopped and the temperature of the reaction quickly dropped to 26° C. GC analysis showed 2.3% NBMeOH and 97.1% NBMeOSiPh$_2$Me. No diphenylmethylsilane was detected. After the reaction mixture stirred another 15 minutes at 25° C., 80 ml saturated aqueous ammonium chloride solution was added. After mixing thoroughly and rinsing with methyl-tert-butyl ether (MTBE), the phases were separated. The aqueous phase gave pH=8. The organic portion was washed with 2×80 ml brine to give pH 10. The organic portion was again washed with 80 ml saturated aqueous ammonium chloride to pH 8, and then washed with 80 ml brine to give between pH 7 and 8. The organic portion was dried over sodium sulfate, filtered, and rotary evaporated to 248.5 g turbid, colorless liquid. GC analysis showed 2.9% NBMeOH, 1.0% Ph$_2$MeSiOH and 1.0% Ph$_2$MeSiO-t-Bu, 95.7% NBMeOSiPh$_2$Me, and 0.1% Ph$_2$MeSiOSiMePh$_2$.

The material was vacuum distilled without the use of a fractionation column. The first 20.8 g was collected between 46-136° C. at 0.27-0.42 Torr to give weight-averaged 30% NBMeOH, 14.3% Ph$_2$MeSiOH/Ph$_2$MeSiO-t-Bu, and 48.5% NBMeOSiPh$_2$Me. The next 71.1 g was collected at 132-139° C. (0.17-0.29 Torr) to give weight-averaged 2.1% Ph$_2$MeSiOH/Ph$_2$MeSiO-t-Bu and 97.6% NBMeOSiPh$_2$Me. The next 7.8 g was collected at 137-134° C. (0.16-0.22 Torr) to give 99.8% NBMeOSiPh$_2$Me. The distillation was stopped and the pot, containing 99.4% NBMeOSiPh$_2$Me, was transferred to the Kugelrohr still. Distillation at 173-176° C. (0.33-0.37 Torr) gave 142.1 g of clear, colorless liquid for 59% yield. GC analysis showed 99.6% NBMeOSiPh$_2$Me.

The GC analysis was performed on a DB5-MS column, 25 m, 0.32 mm ID, 0.52 µm film. Gradient: 75° C. to 200° C. @15° C./min., then heat @40° C./min to 300° C. (3 min. hold); Injector: 200° C. Detector: 350° C. (FID). Retention time: 10.615 minutes.

Comparative Examples 1-5

These Comparative Examples 1-5 demonstrate that reaction of alkenols with CPD results in significant formation of by-products as summarized in Table 1. Most notably, the hydrogenated product, norbornane alkanol, was formed in each of the Comparative Examples 1-5.

Into a suitable high pressure tube reactor were placed various alkenols as co-reactants as summarized in Table 1 and dicyclopentadiene (DCPD) at 4:1 molar ratio based on CPD monomer, and heated in a hot oil bath maintained at 220° C. The batch high pressure tube reactions were run for four hours. At the end of the reaction, the high pressure tubes were removed from the bath and quenched in a wet ice bath. The tubes were washed then with methanol and dichloromethane and weighed to verify that no leakage had occurred. The resultant crude product samples were analyzed by GC-MS. The results are summarized in Table 1.

The GC-MS analysis was performed on an Altech EC-5 column, 30 m, 0.25 mm ID, 0.25 µm film; Inlet-F: 250, MS source: 230° C., electron ionization. The GC conditions used were one of the following two conditions:
a) Gradient: 45° C. to 120° C. at 10° C./min, then heat at 40° C./min to 300° C., hold 2 min at 300° C.—this heating profile was used in Comparative Examples 2 through 5.
b) Gradient: Hold at 40° C. for 5 min., then heat at 40° C./min to 300° C., hold 5 min at 300° C.—this heating profile was used in Comparative Example 1.

TABLE 1

| Comp. Example No. | Alkenol | Product Composition (mole %) |
|---|---|---|
| 1 | Allyl Alcohol | Norbornene methanol (81.2%) |
| | | Allyl alcohol (12.5%) |
| | | (1,2,3,4,4a,5,8,8a-Octahydro-1,4:5,8-dimethanonaphthalen-2-yl)methanol (1.5%) |
| | | CPD trimer (0.3%) |
| | | Norbornane methanol (1%) |
| | | (Decahydro-1,4:5,8-dimethanonaphthalen-2-yl)methanol (0.6%) |
| 2 | But-3-en-1-ol | Norbornene ethanol (76.9%) |
| | | But-3-en-1-ol (8%) |
| | | (1,2,3,4,4a,5,8,8a-Octahydro-1,4:5,8-dimethanonaphthalen-2-yl)ethanol (3.7%) |
| | | CPD trimer (1.7%) |
| | | Norbornane ethanol (1%) |
| | | (Decahydro-1,4:5,8-dimethanonaphthalen-2-yl)ethanol (0.6%) |
| | | DCPD (0.2%) + other impurities |

TABLE 1-continued

| Comp. Example No. | Alkenol | Product Composition (mole %) |
|---|---|---|
| 3 | Hex-5-en-1-ol | Norbornene butanol (50.4%) |
| | | Hex-5-en-1-ol (44.2%) |
| | | (1,2,3,4,4a,5,8,8a-Octahydro-1,4:5,8-dimethanonaphthalen-2-yl)butanol (2.6%) |
| | | CPD trimer (1.5%) |
| | | Norbornane butanol (0.8%) |
| 4 | 2-Methyl-but-3-en-1-ol | 2-Norbornene-2-propanol (48.8%) |
| | | 2-Methyl-but-3-en-1-ol (35.9%) |
| | | (1,2,3,4,4a,5,8,8a-Octahydro-1,4:5,8-dimethanonaphthalen-2-yl)-2-propanol (7.5%) |
| | | 2-Norbornane propanol (0.6%) |
| | | CPD trimer (4.8%) |
| | | DCPD (0.4%) |
| 5 | 2-Methyl-pent-3-en-1-ol | Norbornene isobutanol (52.6%) |
| | | 2-Methyl-pent-3-en-1-ol (40.2%) |
| | | (1,2,3,4,4a,5,8,8a-Octahydro-1,4:5,8-dimethanonaphthalen-2-yl)isobutanol (4.3%) |
| | | Norbornane isobutanol (0.6%) |
| | | CPD trimer (1.9%) |
| | | DCPD (0.12%) |

Comparative Examples 6-7

These Comparative Examples 6-7 demonstrate that reaction of alcohols, such as methanol and isopropanol, with CPD also results in hydrogenation reaction presumably via hydrogen transfer reaction. The results are summarized in Table 2.

Into a suitable high pressure tube reactor were placed various alcohols as co-reactants as summarized in Table 2 and dicyclopentadiene (DCPD) at 4:1 molar ratio based on CPD monomer, and heated in a hot oil bath maintained at 220° C. The batch high pressure tube reactions were run for four hours. At the end of the reaction, the high pressure tubes were removed from the bath and quenched in a wet ice bath. The tubes were washed then with methanol and dichloromethane and weighed to verify that no leakage had occurred. The reaction of methanol with DCPD also produced some insoluble solids. These solids were extracted with dichloromethane (DCM). The DCM extract was then analyzed by GC-MS. The resultant product samples were analyzed by GC-MS. The results are summarized in Table 2.

TABLE 2

| Comp. Example No. | Alcohol | Product Composition (mole %) |
|---|---|---|
| 6 | Methanol | DCPD (37.9%); Dihydro-DCPD (0.2%); CPD trimer (56.4%); CPD tetramer (4%) |
| 6 | Methanol (insoluble extract from dichloromethane) | DCPD (8.3%); Dihydro-DCPD (0.1%); CPD trimer (57.1%); CPD tetramer (21.2%) |
| 7 | Iso-propanol | DCPD (23%); Dihydro-DCPD (0.2%); CPD trimer (56.7%); CPD tetramer (11.9%) |

The GC-MS analysis was performed on an Altech EC-5 column, 30 m, 0.25 mm ID, 0.25 μm film; Inlet-F: 250, MS source: 230° C., electron ionization. The GC conditions used are as follows: Gradient: Hold at 40° C. for 5 min., then heat at 40° C./min to 300° C., hold 5 min at 300° C.

Comparative Examples 8-10

These Comparative Examples 8-10 demonstrate that reaction of alcohols, such as methanol and isopropanol, with norbornene or norbornadiene also results in hydrogenation reaction presumably via hydrogen transfer reaction.

Into a suitable high pressure tube reactor were placed various alcohols and the olefin (norbornene or norbornadiene) at 4:1 molar ratio based on the olefin, and heated in a hot oil bath maintained at 220° C. The batch high pressure tube reactions were run for four hours. At the end of the reaction, the high pressure tubes were removed from the bath and quenched in a wet ice bath. The tubes were washed then with methanol and dichloromethane and weighed to verify that no leakage had occurred. The resultant product samples were analyzed by GC-MS. The results are summarized in Table 3.

TABLE 3

| Comp. Example No. | Olefin | Alcohol | Product Composition (mole %) |
|---|---|---|---|
| 8 | Norbornene | Methanol | Norbornane (0.4%) |
| | | | Norbornene (84.2%) |
| | | | 2-Methoxynorbornane (10%) |
| | | | 1,2,3,4,4a,5,8,8a-Octahydro-1,4:5,8-dimethanonaphthalene (4.6%) |
| 9 | Norbornene | Isopropanol | Norbornane (0.5%) |
| | | | Norbornene (95.4%) |
| | | | 1,2,3,4,4a,5,8,8a-Octahydro-1,4:5,8-dimethanonaphthalene (4.1%) |
| 10 | Norbornadiene | Isopropanol | Norbornadiene (99.2%) |
| | | | Norbornene (0.8%) |

The GC-MS analysis was performed on an Altech EC-5 column, 30 m, 0.25 mm ID, 0.25 μm film; Inlet-F: 250, MS source: 230° C., electron ionization. The GC conditions used one of the following two conditions:
a) Gradient: 45° C. to 120° C. at 10° C./min, then heat at 40° C./min to 300° C., hold 2 min at 300° C.—this heating profile was used in Comparative Examples 8 and 9.
b) Gradient: Hold at 40° C. for 5 min., then heat at 40° C./min to 300° C., hold 5 min at 300° C.—this heating profile was used in Comparative Example 10.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for the preparation of norbornene methanol of formula (IB):

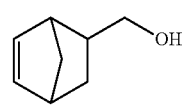

(IB)

comprising:
reacting cyclopentadiene with allyl acetate, without any solvent, at a temperature of from about 130° C. to about 260° C. for a sufficient period of time to form norbornene methyl acetate of formula (IIIB):

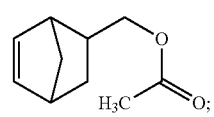

(IIIB)

distilling so formed norbornene methyl acetate of formula (IIIB); and subjecting said distilled norbornene methyl acetate (IIIB) to trans-esterification reaction in the presence of methanol and a catalyst at a temperature of from about 40° C. to about 50° C. to form norbornene methanol (IB) of purity of at least 99 percent, which is essentially free of norbornane methanol.

2. The process of claim 1, wherein cyclopentadiene is reacted with allyl acetate at a temperature of from about 180° C. to about 240° C. and said reaction is carried out in a closed tubular reactor.

3. The process of claim 1, wherein cyclopentadiene is reacted with allyl acetate at a temperature of from about 200° C. to about 240° C.

4. The process of claim 1, wherein cyclopentadiene is reacted with allyl acetate at a temperature of from about 210° C. to about 230° C.

5. The process of claim 1, wherein cyclopentadiene is reacted with allyl acetate at a temperature of about 220° C.

6. The process of claim 1, wherein the catalyst is a base.

7. The process of claim 6, wherein the base is selected from the group consisting of lithium hydroxide, lithium methoxide, lithium ethoxide, lithium tert-butoxide, lithium carbonate, lithium bicarbonate, sodium hydroxide, sodium methoxide, sodium ethoxide, sodium tert-butoxide, sodium carbonate, sodium bicarbonate, potassium hydroxide, potassium methoxide, potassium ethoxide, potassium tert-butoxide, potassium carbonate, potassium bicarbonate, cesium hydroxide, cesium methoxide, cesium ethoxide, cesium tert-butoxide, cesium carbonate, cesium bicarbonate, calcium hydroxide, calcium methoxide, calcium ethoxide, calcium tert-butoxide, calcium carbonate, calcium bicarbonate, magnesium hydroxide, magnesium methoxide, magnesium ethoxide, magnesium tert-butoxide, magnesium carbonate, magnesium bicarbonate, ammonia, trimethylamine, triethylamine, imidazole, and a mixture in any combination thereof.

8. The process of claim 6, wherein the base is sodium methoxide.

9. The process of claim 1, wherein the catalyst is an acid.

10. The process of claim 9, wherein the acid is selected from the group consisting of hydrochloric acid, hydrobromic acid, hydrofluoric acid, sulfuric acid, methanesulfonic acid, trifluoromethanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid, and a mixture in any combination thereof.

11. The process of claim 1, wherein the purity of norbornene methanol (IB) is at least 99.6 percent.

12. The process of claim 1, wherein the purity of norbornene methanol (IB) is at least 99.8 percent.

13. A process for the preparation of (bicyclo[2.2.1]hept-5-en-2-ylmethoxy)(methyl)-diphenylsilane of formula (VB):

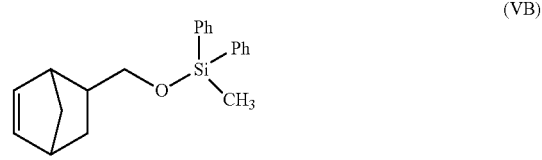 [SMILES: C[Si](OCC1CC2C=CC1C2)(c1ccccc1)c1ccccc1]

comprising:

reacting cyclopentadiene with allyl acetate, without any solvent, at a temperature of from about 200° C. to about 240° C. for a sufficient period of time to form norbornene methyl acetate of formula (IIIB):

subjecting norbornene methyl acetate (IIIB) to trans-esterification reaction in the presence of methanol and sodium methoxide at a temperature of from about 40° C. to about 50° C. to form norbornene methanol (IB), which is essentially free of norbornane methanol:

and reacting norbornene methanol (IB) with methyldiphenylsilane in the presence of a suitable solvent and a catalyst to obtain (bicyclo[2.2.1]hept-5-en-2-ylmethoxy)(methyl)diphenylsilane (VB) of at least 99 percent purity.

14. The process of claim 11, wherein the solvent is tetrahydrofuran.

15. The process of claim 11, wherein the catalyst is potassium tert-butoxide.

16. The process of claim 11, wherein the purity of (bicyclo[2.2.1]hept-5-en-2-ylmethoxy)(methyl)diphenylsilane (VB) is at least 99.5 percent.

17. The process of claim 11, wherein the purity of (bicyclo[2.2.1]hept-5-en-2-ylmethoxy)(methyl)diphenylsilane (VB) is at least 99.8 percent.

* * * * *